United States Patent [19]
Kiovsky et al.

[11] 4,232,181
[45] Nov. 4, 1980

[54] HYDROISOMERIZATION OF PENTANE UTILIZING PD EXCHANGED MORDENITE

[75] Inventors: Joseph R. Kiovsky, Kent; William J. Goyette, Brimfield, both of Ohio

[73] Assignee: Norton Company, Worcester, Mass.

[21] Appl. No.: 53,078

[22] Filed: Jun. 28, 1979

Related U.S. Application Data

[60] Division of Ser. No. 913,812, Jun. 8, 1978, which is a continuation of Ser. No. 825,979, Aug. 19, 1977, abandoned, which is a continuation of Ser. No. 421,505, Dec. 3, 1973, abandoned.

[51] Int. Cl.² ............................................. C07C 5/30
[52] U.S. Cl. ..................................................... 585/739
[58] Field of Search ...................... 585/739; 252/455 Z

[56] References Cited

U.S. PATENT DOCUMENTS

| | | | |
|---|---|---|---|
| 3,190,939 | 6/1965 | Benesi | 585/739 |
| 3,507,931 | 4/1970 | Morris et al. | 585/739 |
| 3,574,092 | 4/1971 | Mitsche | 585/739 |
| 3,836,597 | 9/1974 | Sie | 585/739 |
| 3,842,114 | 10/1974 | Sie | 585/739 |
| 3,932,554 | 1/1976 | Takase et al. | 585/739 |

*Primary Examiner*—George Crasanakis
*Attorney, Agent, or Firm*—Rufus M. Franklin

[57] ABSTRACT

Ammonia exchanged large port mordenite, which is subsequently mildly acid leached, and calcined, in which at least 95% of the exchangeable sodium has been removed and having from 0.38 to 0.8 milliequivalents of acid sites at least as strong as 48% sulfuric acid per gram (as measured by titration with butylamine, and employing dicinnamalacetone indicator) has been found to be highly active hydrocarbon isomerization catalyst. Incorporation of noble metal, e.g. palladium, on the catalyst improves the selectivity for isomerization of normal pentane to isopentane for highly active catalysts at high conversion rates.

1 Claim, No Drawings

HYDROISOMERIZATION OF PENTANE UTILIZING PD EXCHANGED MORDENITE

This is a division of application Ser. No. 913,812, filed June 8, 1978, which was a continuation of U.S. Application Ser. No. 825,979 filed Aug. 19, 1977, now abandoned, which in turn was a continuation of application Ser. No. 421,505 filed Dec. 3, 1973, now abandoned.

FIELD OF THE INVENTION

An improved zeolite catalyst of high acidity for reactions such as the isomerization of normal hydrocarbons, and methods of making and using are taught. Other reactions for which highly acid catalysts are desireable are alkylation and cracking of hydrocarbons.

BACKGROUND OF THE INVENTION

U.S. Pat. Nos. 3,475,345; 3,324,188; and 3,190,939 teach the use of large port hydrogen exchanged mordenite as a catalyst for hydrocarbon isomerization. The first named patent discloses that strong, hot acid leaching followed by mild acid leaching, finally followed by ammonium exchange results in an improved isomerization catalyst as compared to mordenite in which one or more of the 3 steps of the treatment is omitted.

SUMMARY OF THE INVENTION

The process of the present invention involves ammonium exchange of large port mordenite followed by mild acid treatment. Such treatment results in a catalyst more active and selective toward hydrocarbon isomerization than previously known mordenite catalysts. Incorporation of a noble metal into the catalyst further improves its selectively.

The starting material is any large port mordenite such as described in Sand U.S. Pat. No. 3,436,174. As synthesized the material may be in the sodium exchanged form. Other exchange forms however may be employed, the sodium form being employed in the following example merely because it is the commonly available starting material. The ammonium exchange is preferably done with 3 to 5 normal $NH_4+$ solutions at room temperature or at elevated temperatures until 95% or more of the $Na^+$ has been removed. The acid treatment requires 0.1 to 1 N mineral acid at boiling (refluxing) temperature for 1 to 24 hours, preferably for 3 to 5 hours before the product is washed free of acid.

The acid treatment should be such that the silica to alumina ratio of the product is no higher than 17 to 1. The acidity of the zeolite after being washed with water and dried, subsequent to the acid treatment, can be measured by the use of dicinnimalacetone indicator and n-butylamine titrant as described by H. Benesi, J. Phys. Chem. 61, 970 (1957). The treated mordenite of this invention has been found by this method to have a total acidity of acid sites at least as strong as 48% sulfuric acid of from 0.38 to 0.8 milliequivalents per gram ($pK_a$ of minus 3 or lower).

EXAMPLES OF SPECIFIC EMBODIMENTS

EXAMPLE I

The starting material in the following example was large port sodium mordenite, made according to the teaching of U.S. Pat. No. 3,436,174, in pelletized form bonded by a silicious bond. The 1/16" pellets contained 6.1% $Na_2O$, and the silica to alumina mole ratio was 10.5 to 1.

The sodium zeolite was treated with 3 to 5 normal $NH_4NO_3$ solutions until chemical analysis showed a constant 0.27% by weight of $Na_2O$ (on an anhydrous basis). The product was washed free of $NH_4NO_3$ solution by repeated washings with water. Two hundred grams of the washed product was treated by boiling for four hours in 400 ml. of 0.5 normal HCl. After washing free of acid, the product was found to contain 0.23% $Na_2O$, and had a silica to alumina ration of 10.7 to 1, after calcination for 24 hours at a maximum temperature of 550° C.

The testing procedure for isomerization employed a 1 to 1 volume mixture of the mordenite pellets with inert fused alumina aggregate. The process conditions were a temperature of the bed of 480° F., pressure of 450 p.s.i.g., hydrogen to normal pentane feed mole ratio of 7/1 and weight hourly space velocity of 1.00 gram of normal C-5 per gram of catalyst per hour.

The product of this example gave a 30.9% molar conversion to isopentane with 1.62% of the feed cracked (isomer ratio of 0.315, and selectivity of 95%).

EXAMPLE II

Sodium mordenite high purity powder (large port mordenite as disclosed in U.S. Patent 3,436,174) was subjected to a plurality of 3 normal $NH_4NO_3$ exchanges until the soda content was less the 0.1% by weight (on an anhydrous basis). The silica to alumina mole ratio was 10. The washed ammonium exchanged mordenite was then refluxed for 3 hours in 0.5 N HCl, washed free of acid, and calcined as in Example I. The silica to alumina ratio of the product was 13, and the total acidity of acid sites stronger than 48% $H_2SO_4$ was 0.38 milliequivalents per gram. This product was re-exchanged with $NH_4NO_3$ and palladium was introduced by treatment with aqueous tetra-amino palladium chloride, to incorporate about 0.5% by weight of Pd.

Under the same test conditions as Example I this catalyst bonded with 20% by weight of microcrystalline boehmite and calcined as in Example I gave an isomer ratio (fraction of isopentane to $C_5$'s in product) of 0.347 at 97.6% selectivity (iso $C_5$ in product as % of $C_5$ converted), equivalent to a 34.4% conversion and 0.8% cracking of the feed.

EXAMPLE III

Ammonium exchanged mordenite, prepared as in Example II was refluxed 3 hours in 0.34 normal nitric acid, to a silica to alumina ratio of 15.6. After washing and re-ammoniation, 0.5 weight % of palladium was incorporated by tetra ammonium palladium chloride exchange. The powder was then pelletized as in Example II.

The acidity equal to or greater than 48% $H_2SO_4$ was 0.517 meg/gram of mordenite, and when tested for pentane isomerization it gave 44.2% conversion, and, 0.6% cracking, to give an isomer ratio of 0.445 and a selectivity of 98.6%. The isomerization conditions varied slightly from the previous test in that the hydrogen to hydrocarbon mole ratio was 7.1 to 1, and the space velocity was 1.00 cc of normal pentane per cc of catalyst per hour (LHSV=1).

When this catalyst was tested under conditions more amenable to commercial usage, i.e. T=500° F., $H_2/C_5$=1.8, LHSV=1.00, conversion of 64.7%, and cracking of 3.4% was obtained. This corresponds to an isomer ratio of 0.67 and a selectivity of 95%.

EXAMPLES IV TO VII

Ammonium mordenite, prepared as in Example III (prior to acid leaching) was subjected to reflux with 0.34 normal $HNO_3$ for different periods of time, washed, palladium exchanged as in Example II pelletized with 2% temporary organic binder, and calcined as in Example I. The silica to alumina ratios, acidity equal to or greater than 48% $H_2SO_4$, and catalytic performance are given below. The isomerization conditions were; hydrogen to normal pentane mole ratio 1.81/1, LHSV of 1, temperature of 480° F.

| Duration of acid treatment, hours | 1 | 3 | 5 | 24 |
|---|---|---|---|---|
| $SiO_2/Al_2O_3$ mole ratio | 13.0 | 14.7 | 14.6 | 16.3 |
| Acidity $\geq$ 48% $H_2SO_4$ | 0.522 | 0.574 | 0.750 | 0.800 |
| Isomer ratio | 0.362 | 0.478 | 0.450 | 0.346 |
| Selectivity % | 91.3 | 91.9 | 92.7 | 90.6 |
| % Conversion to isopentane | 35 | 45.9 | 43.5 | 33.4 |
| % Cracking | 3.3 | 4 | 3.4 | 3.5 |
| % Unconverted | 61.7 | 50.1 | 53.1 | 63.1 |

The catalyst of this invention yields better selectivity and isomer ratio's than prior art acid treated mordenites in the isomerization of normal paraffins containing 4 to 8 carbon atoms. Suitable conditions for the reaction are a temperature between 450° and 550° F., a pressure between atmospheric and 1000 p.s.i.g., a normal paraffin liquid hourly space velocity of from 0.1 to 10 at a hydrogen to hydrocarbon mole ratio between 0.1 and 10.

The use of a hydrogenation component in the amount of from 0.25 to 1.0 weight percent on the catalyst is desireable to improve and stabilize the selectivity particularly at high conversion conditions. While palladium has been employed in the above examples it is known that other metals such as platinum, rhodium, nickel and rhenium are effective hydrogenation components and therefore also are effective for the same purpose.

What is claimed is:

1. A method of isomerizing comprising passing a mixture of hydrogen and pentane over Pd exchanged mordenite at a temperature between 450° F. and 550° F., characterized in that said mordenite contain less than 0.2% by weight exchanged sodium, has a silica to alumina ratio of between 10 and 17, contains from 0.38 to 0.8 milliequivalents per gram of acid sites stronger than 48% aqueous sulfuric acid.

* * * * *